US008484841B1

(12) United States Patent
Burros et al.

(10) Patent No.: US 8,484,841 B1
(45) Date of Patent: Jul. 16, 2013

(54) METHOD OF FABRICATING A STIMULATION LEAD FOR APPLYING ELECTRICAL PULSES TO TISSUE OF A PATIENT

(75) Inventors: Paul Burros, West Linn, OR (US); Michael DiGiacomo, Portland, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 308 days.

(21) Appl. No.: 13/076,905

(22) Filed: Mar. 31, 2011

Related U.S. Application Data (60) Provisional application No. 61/319,681, filed on Mar. 31, 2010.

(51) Int. Cl.
*H01R 43/00* (2006.01)

(52) U.S. Cl.
USPC .............. 29/857; 29/825; 29/876; 29/877

(58) Field of Classification Search
USPC .......... 29/857, 825, 861, 872, 876–878; 57/6, 57/10, 17, 18
See application file for complete search history.

(56) References Cited

U.S. PATENT DOCUMENTS

| | | | |
|---|---|---|---|
| 2,139,055 A | 12/1938 | Wright et al. | |
| 3,736,739 A | 6/1973 | Walter | |
| 3,934,395 A | 1/1976 | Vryland | |
| 4,484,586 A | 11/1984 | McMickle et al. | |
| 5,138,138 A | 8/1992 | Theilacker | |
| 5,378,234 A | 1/1995 | Hammerslag | |
| 5,979,288 A | 11/1999 | Gallagher et al. | |
| 6,480,747 B2 | 11/2002 | Schmidt | |
| 6,952,616 B2 | 10/2005 | Wessman et al. | |
| 7,146,222 B2 | 12/2006 | Boling | |
| 7,239,922 B1 | 7/2007 | Boogaard et al. | |
| 7,287,366 B2 | 10/2007 | Dye et al. | |
| 7,356,983 B2 * | 4/2008 | Bieszczad et al. | 57/17 |
| 7,555,349 B2 | 6/2009 | Wessman et al. | |
| 7,672,736 B2 | 3/2010 | Boling | |
| 7,698,883 B2 | 4/2010 | Dye et al. | |
| 2002/0143377 A1 | 10/2002 | Wessman et al. | |
| 2005/0027338 A1 | 2/2005 | Hill | |
| 2005/0027339 A1 | 2/2005 | Schrom et al. | |
| 2005/0027340 A1 | 2/2005 | Schrom et al. | |
| 2005/0027341 A1 | 2/2005 | Schrom et al. | |
| 2006/0041295 A1 | 2/2006 | Osypka | |
| 2006/0089691 A1 | 4/2006 | Kaplan et al. | |
| 2006/0089695 A1 | 4/2006 | Bolea et al. | |
| 2006/0089697 A1 | 4/2006 | Cross et al. | |
| 2006/0107644 A1 | 5/2006 | Dye et al. | |
| 2006/0111768 A1 | 5/2006 | Wessman et al. | |
| 2010/0193065 A1 | 8/2010 | Dye et al. | |

* cited by examiner

*Primary Examiner* — Thiem Phan

(57) ABSTRACT

A method of fabricating a stimulation lead comprises:
providing a central insulator member;
helically wrapping a plurality of conductors about the member, by arranging the plurality of conductor wires in groups with an inter-group spacing that is larger than an inter-conductor spacing within each group;
providing an outer insulator layer to form an intermediate lead body assembly;
forming a lead body by heating polymer material of the intermediate lead body assembly to cause insulative material of the lead body to form a solid, fused cylindrical body about the plurality of conductors, which comprise a first conductor, a last conductor, and inner conductors between the first and last conductor, wherein the first and last conductor comprise respective helix diameters that are smaller than the helix diameters of the inner conductors; and
forming a plurality of electrodes and terminals on the lead body that are electrically connected through the plurality of conductors.

12 Claims, 9 Drawing Sheets

METHOD OF FABRICATING A STIMULATION LEAD FOR APPLYING ELECTRICAL PULSES TO TISSUE OF A PATIENT

CROSS-REFERENCE TO RELATED APPLICATIONS

This application claims the benefit of U.S. Provisional Application No. 61/319,681, filed Mar. 31, 2010, which is incorporated herein by reference.

TECHNICAL FIELD

This application is generally related to a method for fabricating a stimulation lead and stimulation lead for applying electrical pulses to tissue of a patient.

BACKGROUND

Neurostimulation systems are devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine typically for the purpose of chronic pain control. Applying electrical energy to the spinal cord associated with regions of the body afflicted with chronic pain can induce "paresthesia" (a subjective sensation of numbness or tingling) in the afflicted bodily regions which can effectively mask the transmission of non-acute pain sensations to the brain.

Neurostimulation systems generally include a pulse generator and one or more leads. The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator.

Each stimulation lead includes a lead body of insulative material that encloses wire conductors. The distal end of the stimulation lead includes multiple electrodes that are electrically coupled to the wire conductors. The proximal end of the lead body includes multiple terminals, which are also electrically coupled to the wire conductors, that are adapted to receive electrical pulses. The distal end of a respective stimulation lead is implanted at the location adjacent or within the tissue to be electrically stimulated. The proximal end of the stimulation lead is connected to the header of the pulse generator or to an intermediate "extension" lead.

The manufacture of stimulation leads is a relatively complex process. Some manufacturing techniques involve wrapping conductor wires with insulative coatings about a mandrel in a helical manner. An example of a system adapted to perform such winding is shown in U.S. Pat. No. 7,287,366, entitled "Method for producing a multielectrode lead," which is incorporated herein by reference. The system described in the '366 patent draws a mandrel through wire wrapping structure. As the mandrel is drawn into a spool, conductor wires are let out in controlled manner by a plurality of "payout carriers."

The plurality of payout carriers are rotated as a group about the mandrel. Also, each payout carrier is rotated independently about its own axis to compensate for twist imparted by the group rotation to minimize the amount of residual force left on the wound wires. The final product in the '366 patent is a product with multiple conductor wires wound about the mandrel in a helical manner. This product is then cut into separate lengths for fabrication of stimulation leads including attachment of electrodes and terminals.

SUMMARY

In one embodiment, a method, of fabricating a stimulation lead for applying electrical pulses to tissue of a patient, comprises: providing a central insulator member including elastic polymer material; helically wrapping a plurality of conductors about the central insulator member, the helically wrapping arranging the plurality of conductor wires in groups with an inter-group spacing that is larger than an inter-conductor spacing within each group; providing an outer insulator layer to form an intermediate lead body assembly; forming a lead body by heating polymer material of the intermediate lead body assembly to cause insulative material of the lead body to form a solid, fused cylindrical body about the plurality of conductors, wherein the lead body is adapted to elastically elongate at low stretching forces upon implantation into the patient, wherein the groups of conductors in the lead body comprise a first conductor, a last conductor, and inner conductors between the first and last conductor, wherein the first and last conductor comprise respective helix diameters that are smaller than the helix diameters of the inner conductors; and forming a plurality of electrodes and terminals on the lead body that are electrically connected through the plurality of conductors.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Figure 1:
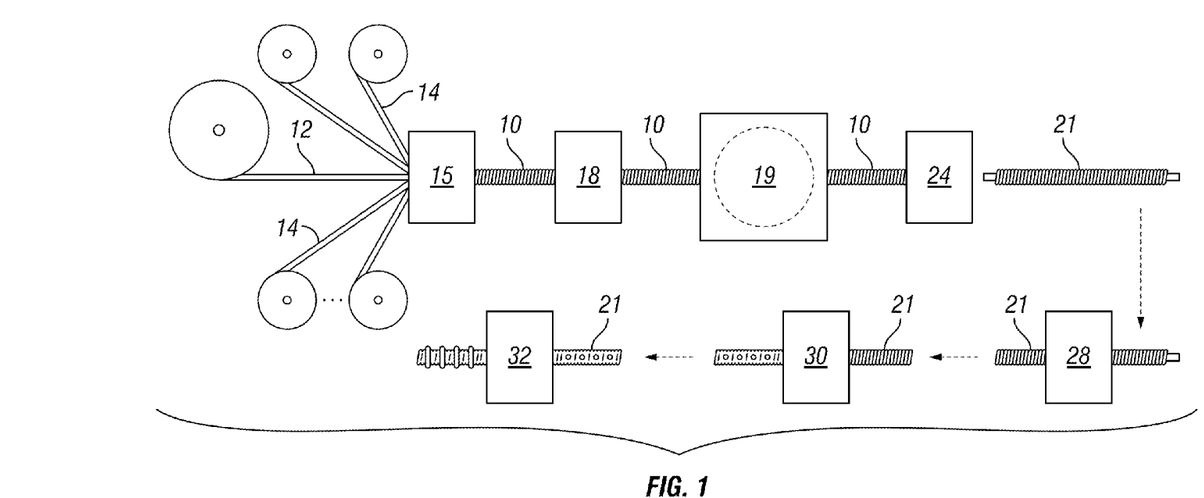
FIG. 1 depicts a process for fabricating a lead body according to one representative embodiment.
Figure 2:
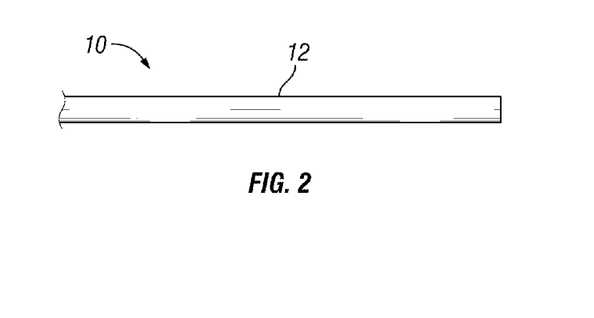
FIG. 2 depicts a mandrel for use in fabricating a lead body.

In one embodiment, a process for fabricating lead body material for stimulation leads begins with a continuous core material 10 shown in FIG. 1. In one embodiment, the core material 10 is a polytetrafluoroethylene (PTFE) coated stainless steel mandrel wire 12 (shown in FIG. 2), although additional insulative layers may also be provided according to other embodiments. Referring again to FIG. 1, the core material 10 is then helically wrapped with a set of insulated wires 14 at a wire wrapping system 15. Each of the wires 14 may include one or more layers of insulation. In one embodiment, each wire 14 comprises an inner thin layer of perfluoroalkoxy (PFA) and outer thicker layer of a thermoplastic silicone polycarbonate urethane (e.g., CARBOSIL™). While eight insulated wires are used in one embodiment, those skilled in the art will recognize that any suitable number of wires may be wrapped onto mandrel 12 according to other embodiments. In other embodiments, additional layers of wires 14 may be wound over the initial layer(s) of wires.

Figure 3:
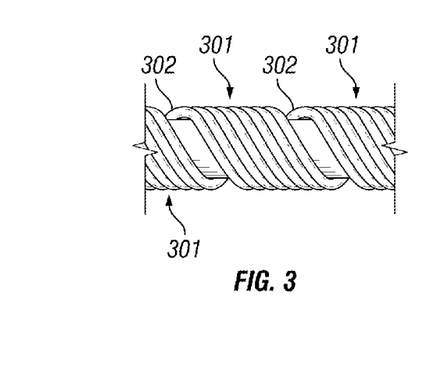
FIG. 3 depicts a segment of a lead body fabricated according to one representative embodiment.

In one preferred embodiment, wires 14 are wrapped about core material 10 in an axially repeating pattern of filar groups 301 of closely spaced wires with each filar group 301 separated by distance 302 that is larger than the spacing between adjacent wires within each group (FIG. 3). The distance between groups in FIG. 3 is by way of example and any suitable distance may be employed according to some embodiments.

Referring again to FIG. 1, core material 10, now comprising mandrel 12 and helically wrapped insulated wires 14 may now be spooled and later unspooled (not shown) or fed directly to the next step in the process. In this next step, core material 10 may be selectively and repeatedly heated in a reflow oven 18. The wires 14 are heated to a temperature that causes the insulation of insulated wires 14 to approach or achieve a phase change, thereby becoming soft and adherent and ultimately fusing together, by heating, melting and re-solidifying after removal from reflow oven 18.

At this point, the core material 10, now comprising mandrel 12 having insulated wires 14 at least partially fused about it, may now be spooled (step 19) onto a spool and stored for later work. Alternatively, step 19 is not performed and core material 10 proceeds directly to the remaining steps. Continuous core material 10 is cut (step 24) into individual lead bodies 21. Each individual lead body 21 may have a length of from about 10 cm (4 in) to about 150 cm (60 in).

After the lead bodies 21 have been cut to length, mandrel 12 is removed from core material 10 (in step 28). This task may be facilitated by a coating of mandrel 12 that will ease removal, such as a PTFE coating. The mandrel removal step 28 may be a simple hand operation by a human worker.

Next, in an electrode creation step 30, electrodes and terminals are provided on the distal and proximal ends of the lead body, respectively. Any suitable technique or process may be employed to provide the electrodes and terminals. Exemplary electrode and terminal fabrication processes are described in U.S. Pat. No. 6,216,045, entitled "Implantable lead and method of manufacture," and U.S. Pat. No. 7,039,470, entitled "Medical lead and method for medical lead manufacture," which are incorporated herein by reference. Also, the lead body could alternatively be connected to a paddle structure which holds electrodes in a planar arrangement as is well known in the art.

Figure 4:
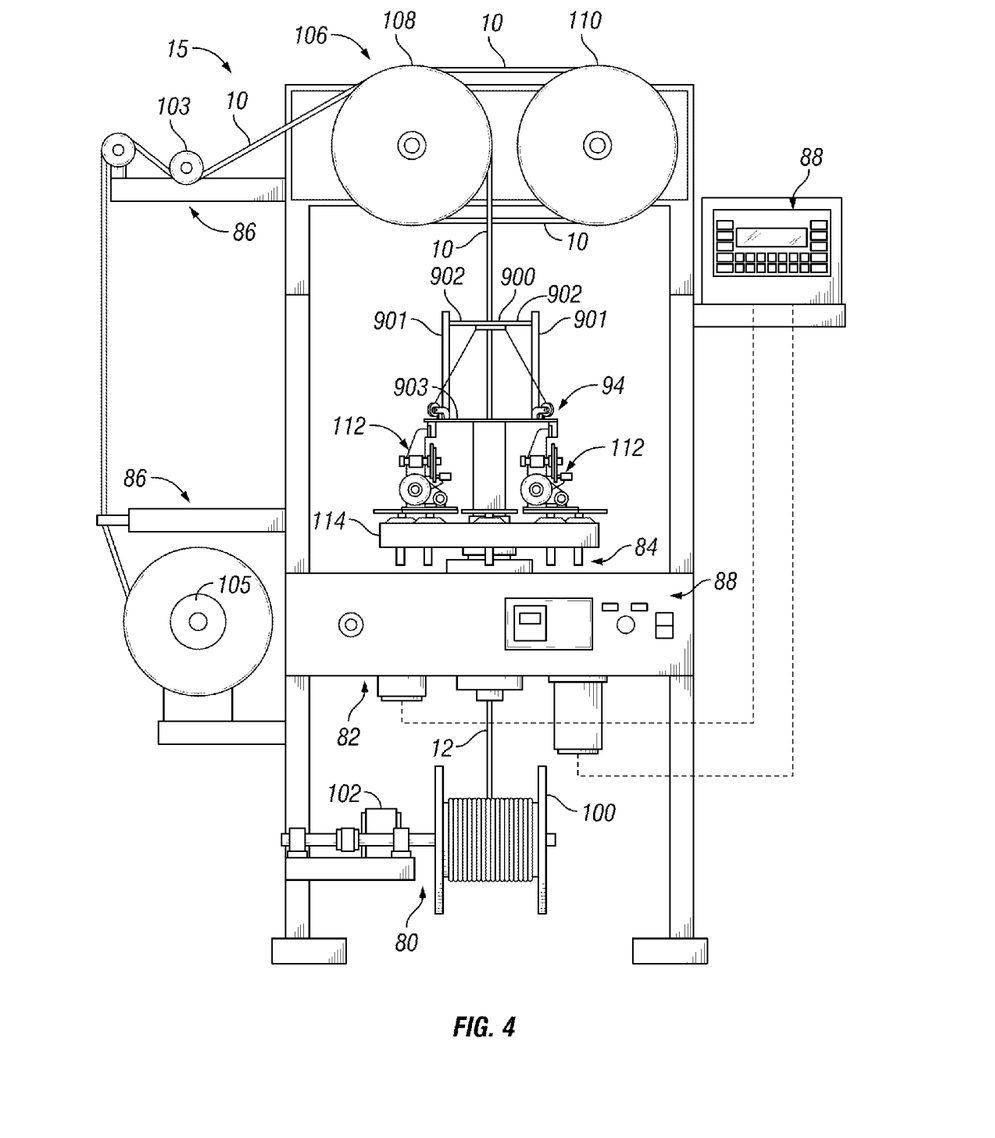
FIG. 4 depicts a wire wrapping system according to one representative embodiment.

Wire wrapping system 15 is shown in greater detail in FIG. 4. Portions of wire wrapping system 15 are omitted from FIG. 4 for the sake of clarity. For example, only two wires are shown in FIG. 4 being wrapped about mandrel 12 and only the corresponding structures for these two wires are shown in FIG. 4. It shall be appreciated that the depicted structures may be duplicated in wire wrapping system 15 in a given implementation according to any suitable number of wires selected to be wrapped about mandrel 12.

The wire wrapping process begins with mandrel payout assembly 80 and core material take up assembly 86 that together maintain core material 10 in well regulated motion and tension along its path. Simultaneously, controls and displays assembly 88 controls a power and linkage assembly 82, which powers a wire payout assembly 84. Although one preferred embodiment permits the use of a keyboard for user input of control parameters, as indicated in FIG. 4, an alternative embodiment provides a simple set of manual controls, such as knobs, for controls and display assembly 88.

Assembly 84 includes turntable 114 upon which a set of payout carriers 112 are supported. Wire wrapping system 15 is configured to permit a variable degree of back twist compensation, which is implemented by rotating carriers 112 relative to turntable 114 at an operator specified rate. In one embodiment, an operator manipulates controls and display assembly 88 to place the right amount of back twist compensation onto wires 14. In an alternative embodiment, the operator enters the wire and mandrel dimensions and the pitch at which the wires are to be wrapped and control and display assembly 88 computes the degree of back twist compensation necessary to prevent residual stress being placed onto wires 14.

Avoiding the placement of residual stress on wires 14 is important so that this stress does not cause the wires to move spontaneously later in the process, causing a deformation in the final shape of the lead body 21, or inconsistent wire locations. After wrapping is complete, wrapped mandrel is spooled by core material take up assembly 86, which maintains a constant tension to avoid deforming the core material 10. In an alternative preferred embodiment, core material 10 is not spooled but progresses immediately to the next stage of processing (e.g., reflow and fusing of the insulative coating material about wires 14).

In greater detail, the progress of core material 10 is maintained by the payout assembly 80 and the take up assembly 86. Payout assembly 80 includes a mandrel payout spool 100, a payout motor 102, and a dancer arm tension measurement device (not shown). Motor 102 is responsive solely to the tension measurement, thereby maintaining constant tension on core material 10. In take up assembly 86, core material take up spool 105 is also motor driven (not shown) and solely responsive to tension measurement dancer arm 103. Take up spool 105 is moved cyclically into and out of the plane of FIG. 4, thereby causing core material 10 to spool in a repeated pattern. The tension placed on core material 10 can be changed by changing the weighting on either dancer arm 103 or the dancer arm of payout assembly 80.

An additional portion of take up assembly 86 is the capstan 106, which includes an equal-diameter pair of wheels 108 and 110, about which core material 10 is looped several times. Each wheel 108 and 110 bears several grooves along its exterior rim, to permit this looping while preventing the core material 10 from ever rubbing against itself. Capstan 106 is driven by an electric motor (not shown) and serves the function of stabilizing core material 10 as it is drawn through the system.

As shown in FIG. 4, core material 10 passes through the center of die 900. Wires 14 pass around one or more radii of die 900. Preferably, die 900 applies force to wires 14 to deform wires 14 for wrapping about core material 10. As shown in FIG. 4, die 900 is held by support struts 902 which are, in turn, coupled to support columns 901.

Figure 10:
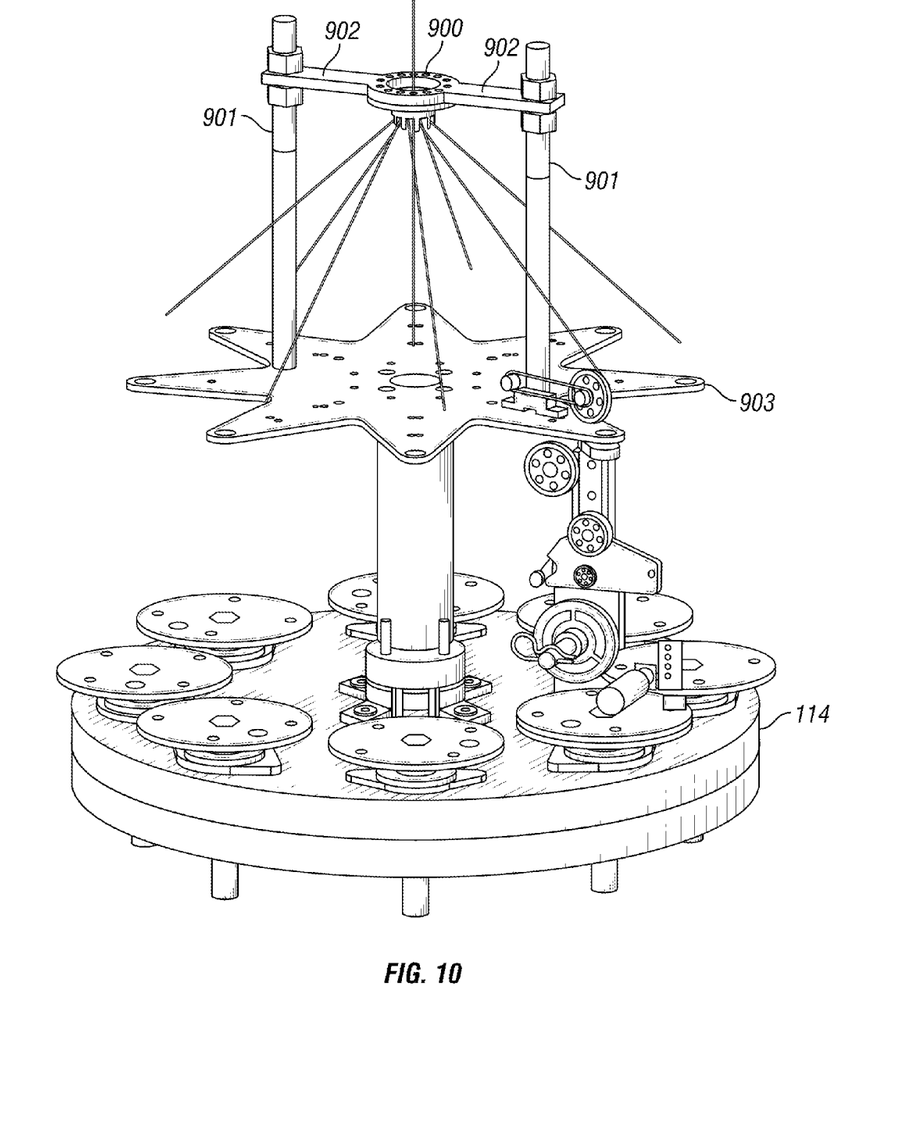
FIG. 10 depicts another view of a wire wrapping system according to one representative embodiment.

Support columns 901 are mounted on platform 903. In one embodiment, platform 903 is mechanically coupled to a drive shaft that is also coupled to turntable 114. Accordingly, platform 903 and die 900 rotate at the same rate as turntable 114. In alternative embodiments, die 900 is not mechanically coupled to turntable 114, but is independently driven to rotate the same rate as turntable 114. An isometric view of die 900 with support struts 902, support columns 901, platform 903, and turntable 114 is shown in FIG. 10.

In some embodiments, wire wrapping system 15 controls the wire wrap pitch using the ratio between the capstan 106 rotation rate and the turntable 114 rotation rate 96 (which equals the rotation rate of a turntable drive motor 132 (FIG. 5) may be set prior to beginning a wire wrapping run. Likewise the backtwist compensation ratio 96, which is the ratio of a payout carrier drive motor 134 rate (FIG. 5) to the turntable drive motor 132 rate, may be set at the same time. Then, during operation, the speed of the entire process may be changed by changing the turntable rotation rate command, which changes the capstan 106 turn rate and payout carrier drive motor 134 rate, automatically. In other words, during operation, the capstan 106 drive and the payout carrier drive motor 134 are slaved to the turntable drive motor 132. The rate of capstan 106 effectively controls the turn rate of take up spool 105 (FIG. 4) and pay out spool 100 (FIG. 4).

Figure 5:
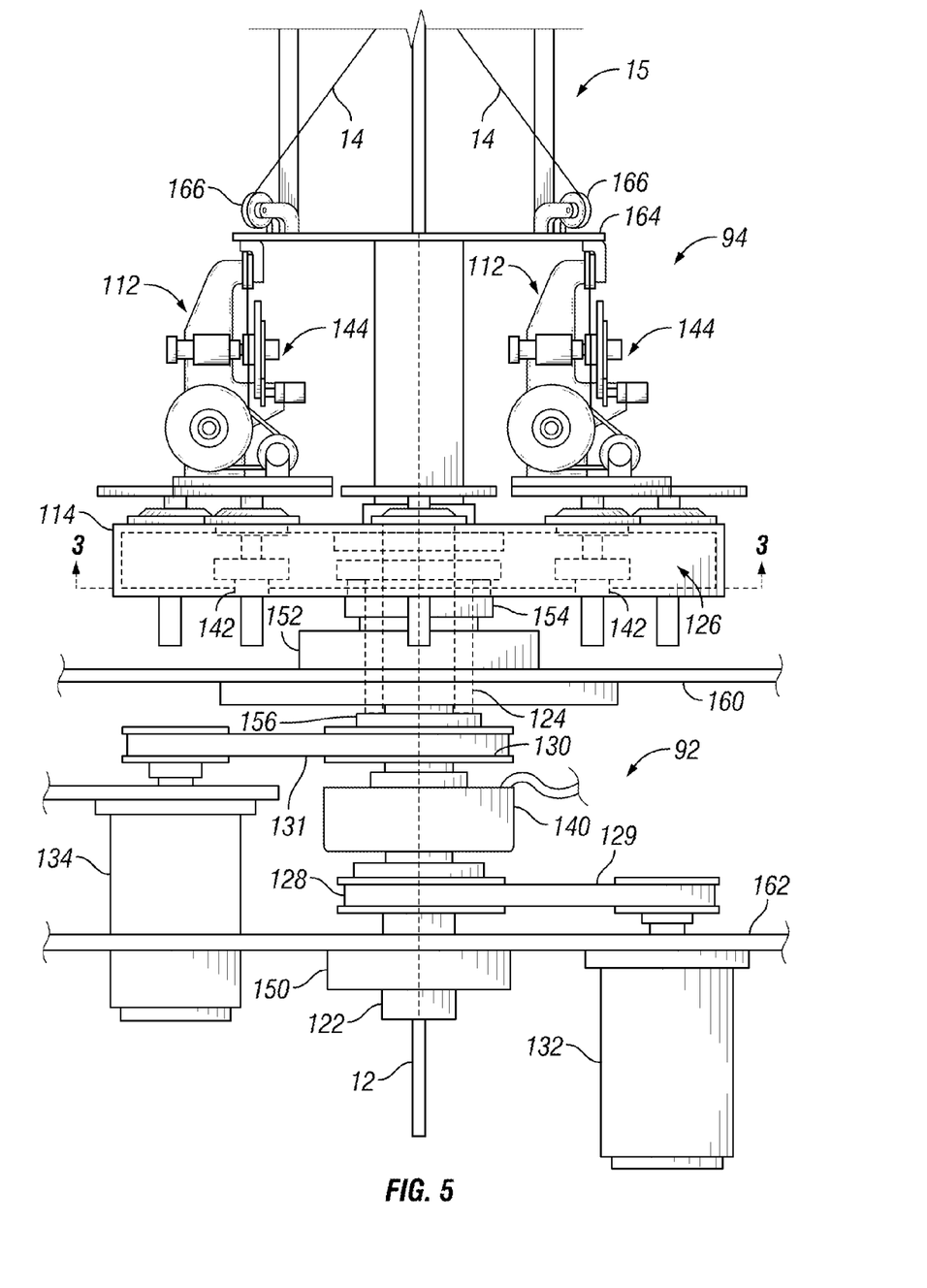
FIG. 5 depicts a portion of the system shown in FIG. 4 according to one representative embodiment.
Figure 6:
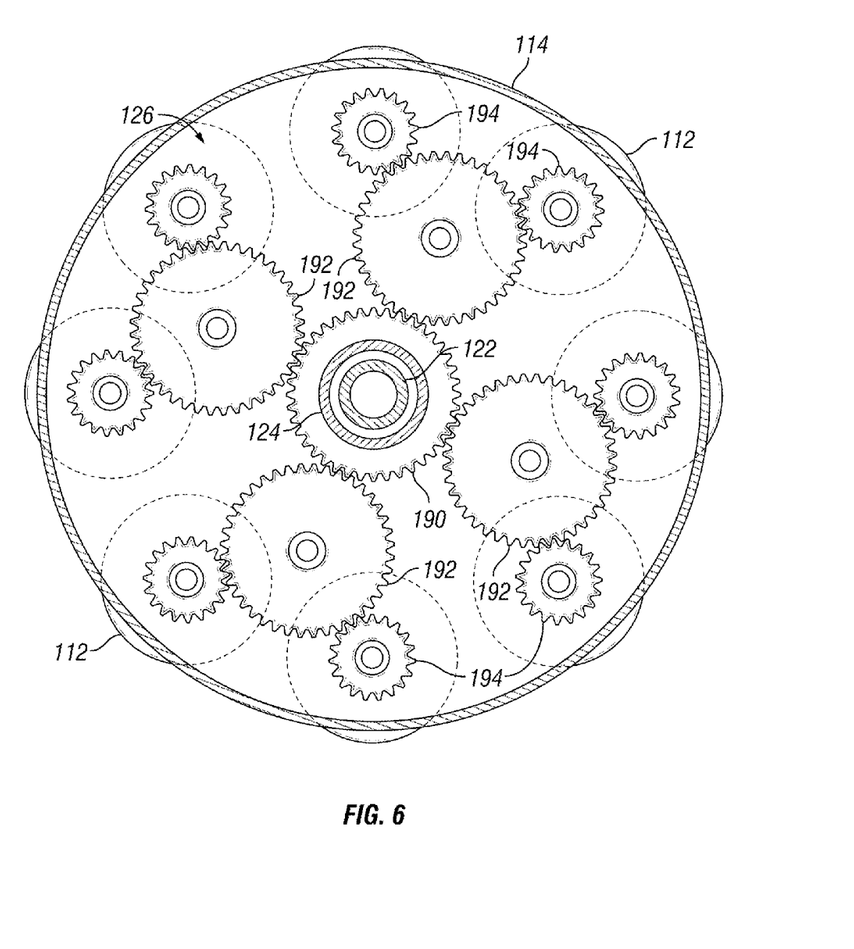
FIG. 6 depicts a set of gears for use in the system of FIG. 4 according to one representative embodiment.

Referring to FIGS. 5 and 6, power and linkage assembly 82 includes an inner shaft 122 which drives the turntable 114, and an outer shaft 124 which drives the payout carriers 112, by way of a system of gears 126. Inner shaft and outer shaft are driven by a first pulley 128 and a second pulley 130, respectively. Each of these pulleys 128, 130 are driven by belts 129 and 131 respectively that are in turn driven by the turntable motor 132 and the payout carrier motor 134, respectively.

The two motors 132 and 134 are managed by the control assembly 88 (FIG. 4), which regulates their relative speed within a range of relative speeds. As noted previously, the turn rate ratio of these two motors is set before a production run is begun. In one preferred embodiment this range extends from equal speed (payout carriers 112 stationary relative to the turntable 114) to the case where the outer shaft rotates at one half the speed of the inner shaft (payout carriers 112 stationary relative to an absolute frame of reference).

A slip ring 140 (shown in FIG. 5) permits electric power to be transmitted to the rotating inner assembly that includes shafts 122 and 124. On turn table 114, each payout carrier 112 includes a slip ring 142 near its base for supplying electricity to the payout carrier 112. Each payout carrier 112 includes an electric wire tension control assembly 144 that maintains a constant tension on the insulated wire 14 that is being threaded onto core material 10. Bearing assemblies 150, 152, 154 and 156 facilitate the rotation of shafts 122 and 124. Plates 160 and 162 support power and linkage assembly 82. A spider 164 supports a wire guide wheel 166 for each payout carrier 112, to further restrain the wires 14 as turntable 114 rotates.

Figure 7:
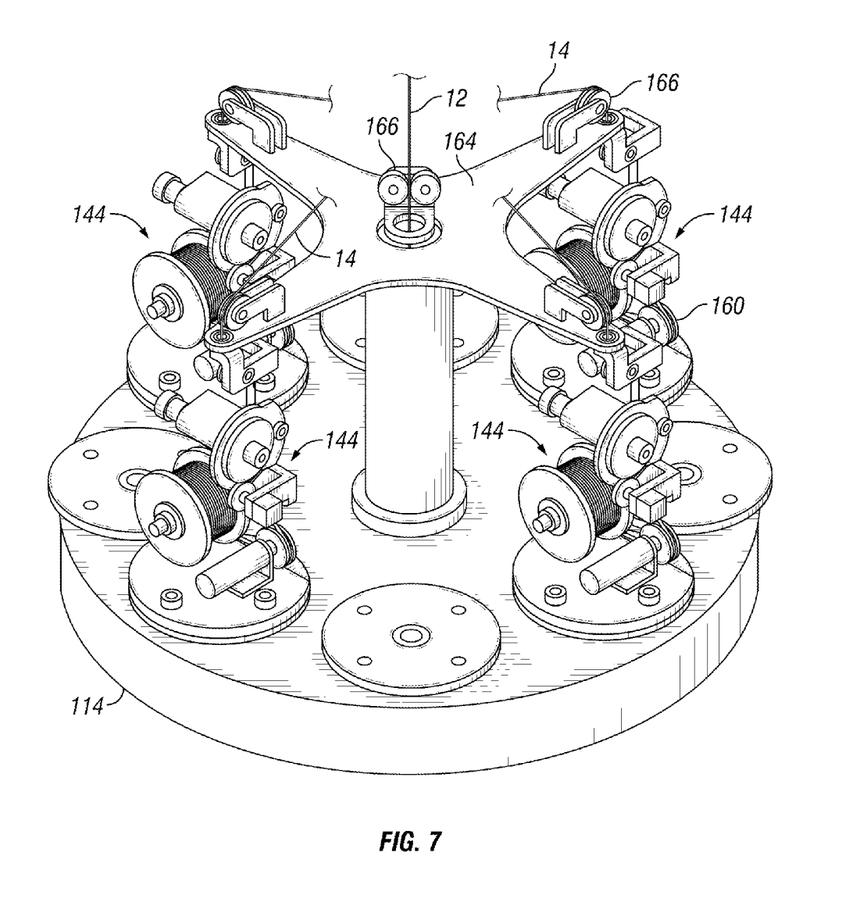
FIGS. 7-9 depict a plurality of payout carriers for use in the system of FIG. 4 according to one representative embodiment.
Figure 8:
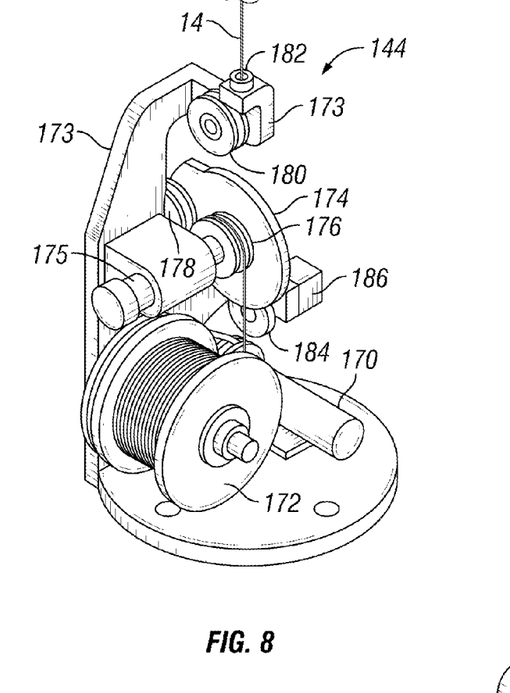
Figure 9:
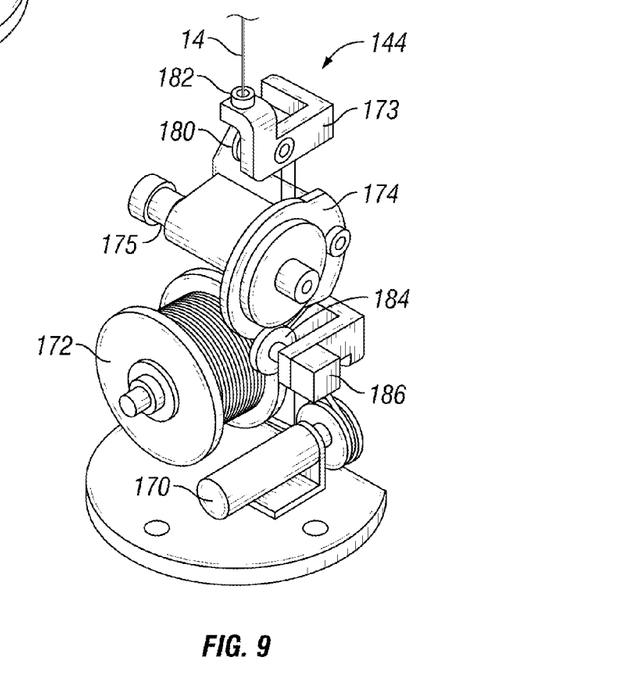

Referring to FIGS. 7-9, each electric wire tension control assembly 144 includes an electric motor 170 that drives a spool 172, both of which are mounted on a payout carrier frame 173. Only four assemblies 144 are depicted in FIG. 7 for the sake of clarity. Any suitable number of assemblies 144 may be included according to some embodiments. A respective wire 14 follows a path defined by a dancer arm 174 which is rotatably mounted by way of an axle 175 to frame 173. Dancer arm 174 has a first dancer arm guide wheel 176 and a second dancer arm guide wheel 178 about which wire 14 is threaded in an "S pattern." Wire 14 proceeds about a frame guide wheel 180 and through a payout carrier exit guide 182. A dancer arm position measurement unit 184 monitors the position of arm 174 and sends this information to an electric motor controller 186. Controller 186 commands the rate at which electric motor 170 turns. This arrangement permits control of the tension in wire 14 to an accuracy of about +1%. In some embodiments, the tension applied when serving the various wires is varied among the wires. Specifically, higher tension is applied to one or more of the wires than the tension applied to the remaining wires to obtain selected characteristics in the fabricated lead body as will be discussed below.

In one embodiment, a lead body is fabricated, in part, using wire wrapping system 15 such that the lead body is capable of elastic elongation under relatively low stretching forces. Also, after removal of the stretching force, the lead body is capable of resuming its original length and profile. For example, in one embodiment, relatively low durometer, elastic polymer material is used for the material of the lead body. The combination of the selection of the materials, the helically wrapping of the wires, and the repeating filar groups with separating gaps enables the stretching according to the relatively low stretching forces. For example, the lead body may stretch 10%, 20%, 25%, 35%, or even up to 50% at forces of about 0.5, 1.0, and/or 2.0 pounds of stretching force. For additional description of a lead body capable of elastic elongation, reference is made to U.S. Patent Publication No. 2007/0282411, entitled "COMPLIANT ELECTRICAL STIMULATION LEADS AND METHODS OF FABRICATION," which is incorporated herein by reference.

Leads manufactured with elastic insulative materials with helically wound groups of wires (referred herein as "compliant leads" for the sake of brevity) exhibit characteristics that substantially deviate from the characteristics of conventional stimulation leads. Initially, compliant leads are well adapted to stretching forces. On a macro-scale, compliant leads elongate in response to a stretching force and return to their prior length upon removal of the force. Over a longer period of time and a large number of stretch/relaxation cycles, a certain percentage of compliant leads may exhibit a wire failure. It has been discovered that, on a micro-scale, polymer dynamics between the wires of an individual group in a compliant lead are more complicated than suggested by a simple elastic model. It is believed that repeated cycles of elongation and relaxation of a lead body may cause deformation of the polymer holding respective wires in place. This deformation, in turn, may apply excessive shearing forces to one or more conductor wires thereby causing a wire failure.

Figure 11A:
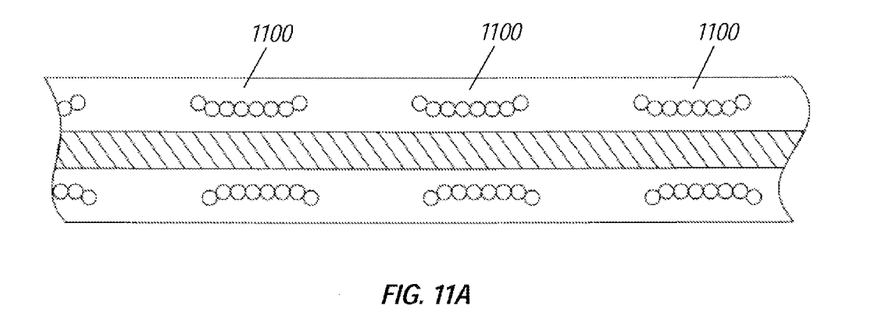
FIG. 11A depicts wires of filar groups in a lead body where a uniform serving tension is applied.

More specifically, when the same tension is employed to serve each wire for a compliant lead, the wires within respective groups 1100 form a "cup" shape as shown in FIG. 11A when viewed in an axial cross section. The outside wires have formed helices with larger diameters than the core wires of each group 1100. When the lead is elongated, the helix diameter of the core wires is reduced more quickly than the helix diameter of the outside wires of each group 1100. This changes the forces applied to the polymer between the outside wires and the adjacent wires from having a compressive component to having a stretching component. Because the polymer does not always completely return to its original shape when the lead is relaxed and then stretched again, the deformation of the polymer may build up over time. The build up of deformation in the polymer may begin to shift the position of the wires relative to each other. That, in turn, results in oscillation of the helix diameter and shearing of a wire when its helix has collapsed.

Figure 11B:
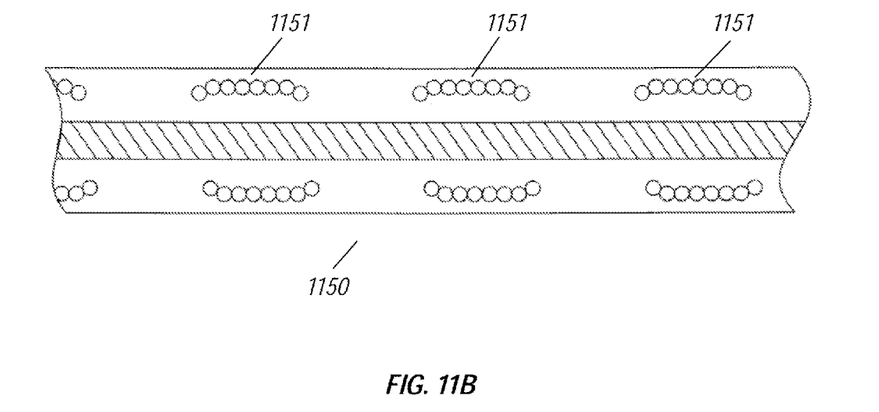
FIG. 11B depicts wires of filar groups in a lead body where a non-uniform serving tension is applied according to one representative embodiment.

In some embodiments, a compliant lead is fabricated such that the outside wires of a filar group have a smaller helix diameter than the helix diameter of the inner wires. When viewed in an axial cross section perspective, the filar groups appear to form a "crown" shape. FIG. 11B depicts lead body 1150 when viewed in an axial cross section according to one representative embodiment. In the embodiment of FIG. 11B, the crown shape is repeated along the length of lead body 1150 in the multiple filar groups 1151.

Using a configuration with the varying helix diameters, the helices of the outside wires in groups 1151 collapse in diameter more quickly than the helices of the inner wires when lead body 1150 is elongated. This variation in diameter between the wires of the filar groups 1151 results in forces that compress the polymer material between the wires of each group 1151. As the polymer is compressed, it builds resistance to additional compression which limits the amount of distortion that the polymer may ultimately experience. As a result, permanent deformation of the polymer is eliminated or mitigated. Lead body 1150 is therefore expected to be less likely to experience a wire failure than other lead body designs.

The crown shape of wires in groups 1151 may be accomplished by serving one wire at a target tension that is greater than the other wires using the previously discussed serving system. The use of a greater serving tension results in the formation of a lead with the wire served at the high tension migrating to one end of the filar group of wires during serving. This higher tension wire is wound with a smaller helix diameter due to the application of the higher tension upon the polymer on the mandrel. Also, the wire at the other end of the filar group indirectly obtains a smaller helix diameter than the helix diameter of the inner wires. This occurs, because the polymer material is compressible and the wire served at the higher tension wire forms a wave of polymer at the point of being served onto the coated mandrel wire. This wave has its greatest effect on wire that is served immediately after the higher tension wire (i.e., the first wire in the next filar group). The first wire in the filar group resists displacement by the wave by pressing down farther into the polymer on the mandrel than the inner wires of the filar group.

In another embodiment, the crown shape of wires in groups 1151 may be accomplished by employing different material coatings on different wires during the serving process. In one embodiment, the inner conductors within the filar groups may be coated with a thicker layer of CARBOSIL™ than the coating applied to the wires on the exterior of the filar groups (e.g., the first and/or last wire in the filar groups). For example, in one embodiment, thicker insulative layers are provided on the inner wires than on the outer wires in the filar groups. In this embodiment, a variation on the serving system may be employed where a die of the serving system controls the positioning of the individual wires. An example of such a system in disclosed in U.S. Provisional Patent Application Ser. No. 61/247,264 entitled "System and method for fabricating a stimulation lead," which is incorporated herein by reference.

Figure 12:
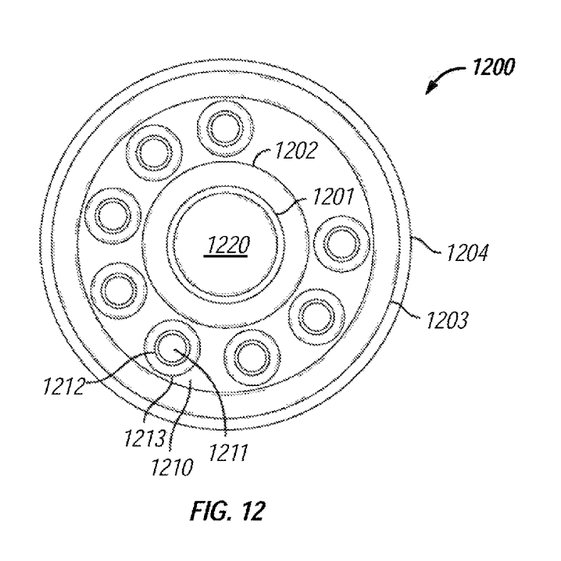
FIG. 12 depicts a cross-sectional view of lead body assembly according to one representative embodiment.

FIG. 12 depicts lead body assembly 1200, viewed in a radial cross section, fabricated according to one representative embodiment to wind one or more wires 1210 with different helix diameters than the remaining wires 1210. Lead body assembly 1200 comprises stainless steel mandrel 1220 which is coated with layer 1201 of PTFE. Inner layer 1202 of CARBOSIL™ is extruded or otherwise provided over the inner layer of PTFE. The mandrel 1220 with layers 1201 and 1202 is utilized as core material 10 in wire wrapping system 15. Wire wrapping system 15 wraps a plurality of wires 1210 about mandrel 1220, layer 1201, and layer 1202. Also, each wire 1210 (only one wire is annotated in FIG. 12 for the sake of clarity) is preferably stranded wire coated with a thin layer of PFA and a thicker layer of CARBOSIL™. One or more selected wires 1210 may be served at a higher tension relative to the other wires 1210. Alternatively, one or more selected wires 1210 may possess thicker layer 1202 than the remaining wires 1210. An outer layer 1203 of CARBOSIL™ is also provided. Shrink wrap tubing 1204 is then provided on the exterior of the assembly.

Figure 13:
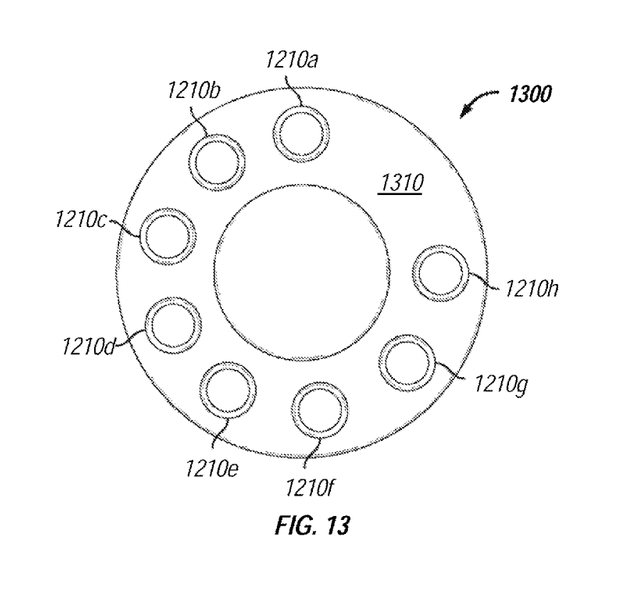
FIG. 13 depicts a lead body fabricated according to one representative embodiment.

Lead body assembly 1200 is subjected to heating above the melting point of the thermoplastic material. The heat and pressure (e.g., from heat shrinkable tubing) causes the thermoplastic insulative material (e.g., the CARBOSIL™ material) to flow. After the thermoplastic material is cooled, the thermoplastic material re-solidifies into a lead body 1300 of fused insulative material enclosing the respective conductors 1210 (individually annotated as wires 1210*a*-1210*h*). Wires 1210*a*-1210*h* exhibit a crown shape when viewed in an axial cross section view. As seen in FIG. 13 in a radial cross section view, wires 1210*a* and 1210*h* are closer to the central axis of lead body 1300 than inner wires 1210*b*-1210*g*. Also, as shown in FIG. 13, gap 1310 is provided within lead body 1300 where no conductors are located within gap 1310. That is, gap 1310 is entirely filled with insulative material.

Figure 14:
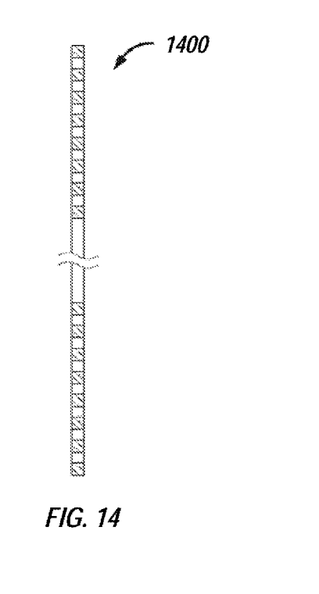
FIG. 14 depicts a stimulation lead fabricated according to one representative embodiment.

Lead body 1300 is then cut into appropriate lengths and electrodes and terminals are provided using any known or later developed process to form stimulation lead 1400 as shown in FIG. 14. Although lead 1400 is shown fabricated as a "percutaneous lead," other lead designs may also be employed such as paddle-style leads. Also, although some embodiments have discussed fabrication of neurostimulation leads, other medical leads may be fabricated according to other embodiments, such as cardiac leads, mapping leads, ablation leads, etc.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A method of fabricating a stimulation lead for applying electrical pulses to tissue of a patient, the method comprising:

providing a central insulator member including elastic polymer material;

helically wrapping a plurality of conductors about the central insulator member, the helically wrapping arranging the plurality of conductor wires in groups with an inter-group spacing that is larger than an inter-conductor spacing within each group;

providing an outer insulator layer to form an intermediate lead body assembly;

forming a lead body by heating polymer material of the intermediate lead body assembly to cause insulative material of the lead body to form a solid, fused cylindrical body about the plurality of conductors, wherein the lead body is adapted to elastically elongate at low stretching forces upon implantation into the patient, wherein the groups of conductors in the lead body comprise a first conductor, a last conductor, and inner conductors between the first and last conductor, wherein the first and last conductor comprise respective helix diameters that are smaller than the helix diameters of the inner conductors; and forming a plurality of electrodes and terminals on the lead body that are electrically connected through the plurality of conductors.

2. The method of claim 1 wherein the helically wrapping comprises:

controlling a respective tension at which each conductor of the plurality of conductors is wrapped about the central insulator member.

3. The method of claim 2 wherein the last conductor is wrapped at a tension that is higher than one or more tensions employed for wrapping the inner conductors.

4. The method of claim 3 wherein the first conductor is wrapped at a tension value equal to a tension employed for the inner conductors.

5. The method of claim 1 wherein the helix diameter of the last conductor is less than the helix diameter of the first conductor.

6. The method of claim 1 wherein the lead body is capable of elongating more than 20% under a stretching force of less than 3 lbs.

7. The method of claim 1 wherein the lead body is capable of elongating more than 20% under a stretching force of less than 0.5 lbs.

8. The method of claim 1 wherein the lead body is capable of elongating more than 50% without damaging the plurality of conductors.

9. The method of claim 1 wherein the plurality of conductors comprise stranded wire with one or more coatings of insulative material before being wrapped about the central insulator member.

10. The method of claim 9 wherein the one or more coatings of insulative material comprises perfluoroalkoxy (PFA).

11. The method of claim 9 wherein the one or more coatings of insulative material comprises a thermoplastic silicone polycarbonate urethane.

12. The method of claim 11 wherein a thickness of the thermoplastic silicon polycarbonate urethane is greater on the inner conductors than a thickness of the thermoplastic silicon polycarbonate urethane on the first conductor while the helically wrapping is performed.

* * * * *